(12) United States Patent
Bigus et al.

(10) Patent No.: US 6,845,881 B1
(45) Date of Patent: Jan. 25, 2005

(54) DEVICE FOR HANDLING, TRANSPORTING AND STORING CAPILLARIES, METHOD FOR THE PRODUCTION THEREOF AND INDIVIDUAL CAPILLARY DISPENSER THEREFROM

(75) Inventors: Hans Jürgen Bigus, Pliezhausen (DE); Reinhard Frey, Ilsfeld (DE); Hans Rieker, Eberstadt (DE)

(73) Assignee: Hirschmann Laborgeräte GmbH & Co. KG, Eberstadt (DE)

( * ) Notice: Subject to any disclaimer, the term of this patent is extended or adjusted under 35 U.S.C. 154(b) by 51 days.

(21) Appl. No.: 10/031,699

(22) PCT Filed: Jun. 29, 2000

(86) PCT No.: PCT/DE00/02191
§ 371 (c)(1),
(2), (4) Date: Jan. 23, 2002

(87) PCT Pub. No.: WO01/08803
PCT Pub. Date: Feb. 8, 2001

(30) Foreign Application Priority Data

Jul. 29, 1999 (DE) .......................................... 199 35 634

(51) Int. Cl.⁷ .......................... B23Q 7/04; B65G 59/00; B65H 3/28; B65H 5/00; G07F 11/16
(52) U.S. Cl. ...................... 221/210; 221/221; 221/224; 221/226; 221/279; 221/197; 221/25; 42/49.01; 42/50

(58) Field of Search .................. 221/210, 222, 221/224, 226, 279, 195, 25, 221, 197; 42/49.01, 50

(56) References Cited

U.S. PATENT DOCUMENTS

| | | | |
|---|---|---|---|
| 2,139,886 A | * 12/1938 | Drachenberg | 221/186 |
| 3,173,728 A | 3/1965 | Sheer | |
| 3,306,494 A | 2/1967 | Castner | |
| 3,478,923 A | * 11/1969 | Fisher | 221/70 |
| 4,236,637 A | * 12/1980 | Castner et al. | 206/467 |
| 4,550,857 A | * 11/1985 | Castner, Sr. et al. | 221/70 |
| 4,960,566 A | 10/1990 | Mochida | |
| 5,067,629 A | 11/1991 | Schwarz | |
| 5,840,573 A | 11/1998 | Fields | |
| 5,860,561 A | * 1/1999 | Saldana et al. | 221/25 |
| 5,900,132 A | * 5/1999 | Keenan et al. | 204/603 |

FOREIGN PATENT DOCUMENTS

| | | |
|---|---|---|
| DE | 30 46 080 | 6/1982 |
| WO | WO 98 36 995 | 8/1998 |

* cited by examiner

Primary Examiner—Donald P. Walsh
Assistant Examiner—Michael E. Butler
(74) Attorney, Agent, or Firm—Paul Vincent

(57) ABSTRACT

Device for handling, transporting and storing capillaries, method for the production thereof and individual capillary dispenser therefrom.

9 Claims, 1 Drawing Sheet

DEVICE FOR HANDLING, TRANSPORTING AND STORING CAPILLARIES, METHOD FOR THE PRODUCTION THEREOF AND INDIVIDUAL CAPILLARY DISPENSER THEREFROM

BACKGROUND OF THE INVENTION

Use of Adhesive Tape for Handling, Transporting and Storing Capillaries and Dispenser for Individual Capillaries on That Adhesive Tape.

The invention concerns handling, transport and storing of a plurality of capillaries as well as a dispenser of individual capillaries.

Capillaries, in particular microcapillaries are used for a plurality of chemical, biological, biochemical or medical experiments, such as chemical analyses, syntheses, sample preparations, biological tests, blood tests or the like. They consist of an inert material, preferably of glass, and are produced from endless capillary tubes by cutting to length. They are mostly cylindrical, in particular circular cylindrical and the capillary tube can be open at both ends or be closed at one end like a test tube. In the latter case, they can be used as micro-reaction containers and optionally also be coated at the inside with a reactive material, e.g. a catalyst and/or have a flared flange in the region of the fill hole to be closed by a flared cap. Capillary tubes which are open at both ends can also be coated with chromatographic or biologically active sorbents. Also known are capillaries with two closed ends which can be optionally opened via breaking points. The invention concerns such capillaries and micro-reaction containers.

Capillaries are difficult to handle, in particular due to their small size and fragility, both during manual and automated operation for packing, transporting and storing and also utilization by the user. The capillaries which are cut from the endless capillary tube have been conventionally packed in loose bundles. Transport and storage of such loose bundles can lead to breakage and corresponding injuries. The removal from the bundle and positioning of the capillaries is cumbersome and inconvenient, in particular for containers which are closed at one end and must be disposed with the filling hole facing upwards. Automated removal, sorting and positioning is also problematic.

Insertion of the capillaries into corrugated supports or into punched supports of cardboard has been proposed. This is also inconvenient and unsuitable in particular for very fine microcapillaries having a storage capacity of less than several $\mu$l. One has also attempted to detachably interconnect capillaries by coating them with resins, lacquers or the like and by gluing. These efforts do not produce satisfactory results, since the coating sticks to the capillaries and is difficult to remove.

U.S. Pat. No. 4,960,566 discloses a chemical reaction or measuring device to which capillaries, serving as reaction vessels, can be sequentially fed by means of an endless carrier band. The capillaries are disposed in parallel and at equal separations on the carrier band by placing them in slots disposed on the upper run of the endless band, in parallel and extending transverse to the direction of travel of the carrier band. In one embodiment, the capillaries are permanently glued to a support band made from paper and plastic.

It is the underlying purpose of the invention to propose means for simplified handling of capillaries to protect them from breakage, in particular, during transport and storage thereof. The invention is also directed to a dispenser for individual capillaries from those means.

The first part of this task is achieved in accordance with the invention through use of at least one adhesive tape as means for handling, transporting and storing a plurality of capillaries, wherein the capillaries are introduced, in substantially parallel alignment and at separations less than their diameters, onto an endless adhesive tape extending substantially perpendicular to their longitudinal axes to be held thereby at a portion of their outer surfaces, the width of the adhesive tape being smaller than half the length of the capillaries.

SUMMARY OF THE INVENTION

The inventive adhesive tape facilitates fixing, simultaneous orientation and also dispensing of the capillaries by removing the adhesive tape from the capillaries by exercising a small tensile force. The adhesive tape is preferably connected to only a small surface area of the capillaries through substantially tangential attachment of parallel capillaries and extends through less than half the length of the capillaries. When the adhesive tape is removed, only small tensile forces act on the capillaries and even very fine capillaries having a storage capacity of a few $\mu$l do not break. The tight, parallel arrangement of all capillaries largely protects them from premature breaking during packing, storing and transport. The protection against fracture is larger the tighter the arrangement of the capillaries. Only little packing material is required since the capillaries, arranged in parallel and preferably very close to one another, require less space than in a loose bunch. The packing volume can be further reduced and the protection against fracture further increased when the adhesive tape and the capillaries are wound together into a roll or disposed and packed in parallel layers. Their orientation and positioning also simplifies handling by the user. If the capillaries are closed at one end (i.e. micro-reaction containers) their filling holes are preferably oriented in the same direction.

The adhesive tape is preferably coated with a contact adhesive. The contact adhesive can be applied to the tape e.g. as a solution or a dispersion, with the capillaries then being adhesively bonded to the adhesive film and the solvent subsequently evaporated. Such contact adhesives form, within a relatively short time, an adhesive film of sufficient stability for connecting only a small surface area of the capillaries in a substantially tangential manner and guarantee release of the adhesive tape without affecting the capillaries. The adhesive tape is preferably formed as a sheet, e.g. a thermoplastic sheet.

As stated above, the width of the adhesive tape is smaller than half the length of the capillaries and preferably approximately one third of the length of the capillaries. This limits the adhesive strength to a required degree for sufficient adhesion to the tape.

As mentioned above, the capillaries are densely disposed on the adhesive tape, with their separations being smaller than their diameter. They can also abut one another. In this latter case, preferably one or more adhesive tapes are provided on only one side of the parallel capillaries to permit winding about a winding axis at the adhesive tape side.

The central longitudinal region of the capillaries is preferably disposed on one single adhesive tape and projects past both sides of the tape. Alternatively, two or more adhesive tapes can be provided at a separation from one another, with the ends of the capillaries projecting past the outer edges of the adhesive tapes.

To facilitate removal, the adhesive tape has an adhesive-free removing tab at at least one end. The removal tab of the adhesive tape can either be uncoated or the adhesive film can be laminated in the region of the removal tab. The adhesive tape and/or the removal tab can comprise a label, an imprint or the like for identifying the capillaries to indicate e.g. the length, diameter, volume and material.

The invention is fundamentally suited for capillaries of any type, but preferably for capillaries having a small storage capacity of between 0.2 and 500 μl or a capillary diameter of less than 3 nm.

The invention also concerns a dispenser for individual capillaries on an adhesive tape of the above mentioned kind. In accordance with the invention, a dispenser of this kind has at least one substantially U-shaped recepticle for the capillaries whose U-legs are separated by at least the length of the capillaries to guide the ends of the capillaries and with at least one upwardly disposed guide member having a separation from the bottom part of the U-shaped recepticle corresponding approximately to the diameter of the capillary, wherein a slotted guide is fashioned between the bottom of the U-shaped receptacle and the guide member as an abutment for the capillaries which leaves the adhesive tape accessible, into which the capillaries and adhesive tape can be introduced, and which has a dispensing location for the capillaries opposite that introductory location, wherein the adhesive tape can be removed from the capillaries while they are supported in the slotted guide.

After manual removal of the adhesive tape from the capillaries, the capillaries are maintained in parallel arrangement for separation and delivery. Individual capillaries can be removed from the dispenser at the dispensing location with constant predetermined alignment and orientation. The dispenser provides safe and regulated supply of the capillaries and provides protection from mechanical loads. The slotted guidance must be designed such that the capillaries have sufficient support to reliably prevent breakage thereof when removing the adhesive tape.

U.S. Pat. No. 3,173,728 A discloses a dispenser for swabs which are disposed at a middle section thereof on one side of a support strip. A second corrugated strip is also preferably provided to accept the swabs in the corrugations for holding therein by the oppositely disposed support strip. The corrugated strip is guided inside the dispenser using deflecting rollers with the support strip projecting out of the dispenser through a removal opening to dispense the swabs by pulling on the support strip and subsequent release of the swabs therefrom. Individual separation of capillaries is not envisioned and the removal of the swabs is problematic, since these must first be withdrawn from the dispenser and, following withdrawal, separated from the support strip. Moreover, the guided slot of the dispenser in accordance with the invention for individual capillaries permits removal of the adhesive tape prior to dispensing the capillaries and directly after loading the dispenser therewith, so that e.g. the large number of capillaries needed for chemical analysis and synthesis can be rapidly and reliably dispensed.

The arrangement of the guiding member with respect to the U-shaped receptacle depends on the arrangement of the adhesive tape(s) with respect to the longitudinal axis of the capillaries. Towards this end, in a preferred embodiment, two guiding members are provided which face one another and are disposed substantially symmetrically and at a respective U-shaped leg of the receptacle to define an intermediate space for removing the adhesive tape disposed in the central longitudinal region of the capillaries. Both ends of the capillaries are held in the receptacle by the guiding members and the adhesive tape can be removed between the guiding members. The width of the guiding members corresponds preferably to e.g. a third of the length of the capillaries and the width of the adhesive tape disposed at the central longitudinal region of the capillaries corresponds to approximately also a third of the length of the micro-reaction containers.

In a modified embodiment, a central guiding member is disposed at a separation from the U-shaped legs of the receptacle which forms one free space between each of its longitudinal edges and a respective U-shaped leg of the receptacle for removing two adhesive tapes which are disposed at a separation from one another.

A slider is preferably provided which is guided in the slotted guidance and elastically acts on the capillaries in the direction of the dispensing location to constantly load the capillaries in the direction of the dispensing location.

For supplying the dispenser, the slider can be arrested e.g. preferably at the end of the U-shaped bar of the receptacle facing away from the dispensing location. The slider can be connected to a guiding pin which is provided in a slotted hole formed in the U-shaped leg of the receptacle and accommodates a helical spring disposed between the slider and the end of the slotted hole facing away from the dispensing location.

In accordance with another embodiment, the capillaries are wound into a roll and are loaded into and within the slotted guidance in dependence on the amount of capillaries to be dispensed and also using a helical spring cooperating with the winding axle.

In a preferred embodiment, the capillaries can be removed from the dispenser in their axial direction at the dispensing location. In this case, the dispensing location can have at least one delivery opening disposed at the level of the capillaries and penetrating through at least one of the U-shaped legs of the receptacle, whose diameter is preferably approximately equal to or slightly larger than the diameter of the capillaries.

Embodiments of the invention are described in more detail below with reference to the drawings.

BRIEF DESCRIPTION OF THE DRAWING

FIG. 4 shows a front view of a further embodiment of a

DESCRIPTION OF THE PREFERRED EMBODIMENT

Figure 1:
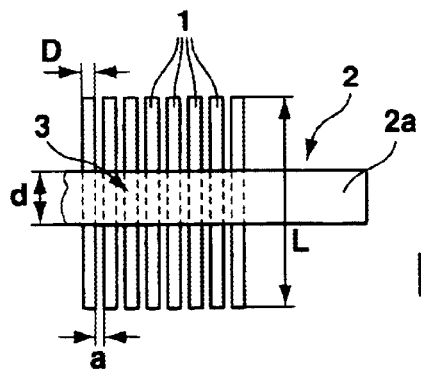
FIG. 1 shows an adhesive tape having an adhesive tape introduced at the longitudinal middle region of the capillaries.

FIG. 1 shows an embodiment in accordance with the invention for use of an adhesive tape 2 to handle, transport and store capillaries 1. The capillaries 1 are arranged in parallel on which extends substantially perpendicular to their longitudinal axes and are thereby held along a portion of their surface area. The adhesive tape 2 is coated with a contact adhesive. The capillaries 1 are disposed close to one another such that the separation a is considerably smaller than the diameter D of the capillaries 1. The diameter D of the capillaries 1 can e.g. be approximately 0.5 mm and the length L approximately 3 cm. In the present embodiment, the width d of the adhesive tape 2 corresponds to approximately 30% of the length L such that the adhesive tape 2 provides sufficient force for holding the capillaries 1 and permits easy removal of the adhesive tape 2. The adhesive tape 2 has a removal tab 2a at at least one end thereof and can be provided in the region of the capillaries 1 and/or the region of the removal tab 2a with labels, imprints 3 or the like for identifying the capillaries 1. The imprint 3 shown indicates e.g. the diameter D and the filling volume V of the capillaries 1. The unit which consists of the adhesive tape 2 and the capillaries can be wound into a roll.

Figure 2:
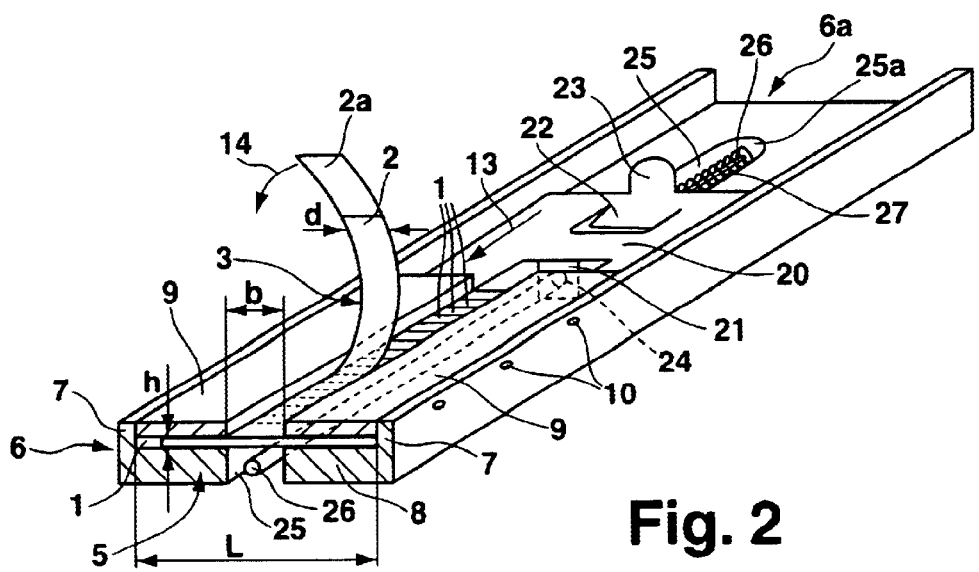
FIG. 2 shows a perspective sectional view of a dispenser for dispensing capillaries from the device in accordance with FIG. 1.

FIG. 2 shows a dispenser for delivering the capillaries 1. It has a slotted guidance 5 into which the capillaries 1, held by the adhesive tape 2, can be introduced. The slotted guidance 5 has a substantially U-shaped receptacle 6 with a U-shaped bar 8 forming a supporting surface for the capillaries 1 and U-shaped legs 7 guiding the ends of the capillaries. The separation between the U-shaped legs 7 therefore corresponds to approximately the length L of the capillaries 1. Two mutually opposed and symmetrically disposed guiding members 9 are each located at a respective U-shaped leg 7 and have a separation from the U-shaped bar 8 of the receptacle 6 corresponding substantially to the diameter D of the capillaries 1. The guiding members 9 are fastened to the U-shaped legs 7 e.g. using rivets 10 and are disposed at a separation b from one another. The separation b corresponds approximately to the width d of the adhesive tape 2 disposed on the central longitudinal region of the capillaries 1. After the capillaries 1 have been inserted into the slotted guidance 5, the adhesive tape 2 can be removed along the guiding members 9 in the direction of the arrow 14. The slotted guidance 5 comprising the receptacle 8 and the guiding members 9 can also be designed as one single C-shaped part.

An elastically supported slider 20 is guided in the slotted guidance 5 which constantly loads the capillaries 1 in the direction of a dispensing location of the dispenser (arrow 13). To facilitate supply of capillaries 1 to the slotted guidance 5, the slider 20 can be arrested at the end 6a of the receptacle 6 facing away from the dispensing location. Towards this end, a tab 22 is punched out of the slider, which consists e.g. of sheet metal, and engages in the end 6a of the receptacle 6. The slider 20 is also provided with a handling means having the shape of a nose 23 which is bent upwards. The elastic support for the slider 20 is realized in the embodiment shown in that the slider 20 has a tab 21 which projects substantially perpendicularly downward and has a bore 24 which is penetrated by a guiding pin 26 disposed in a slot in the U-shaped bar 8 of the receptacle 6. A helical spring 27 is disposed on the guiding pin 26 between the tab 21 and the end of the slot 25a facing away from the dispensing location.

Figure 3:
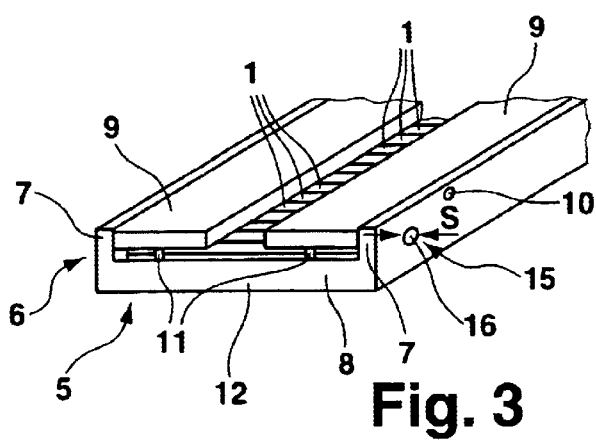
FIG. 3 shows a perspective detailed view of the dispensing location of the dispenser in accordance with FIG. 2.

As seen in FIG. 3, the capillaries 1, loaded by the helical spring 27 in the direction of the dispensing location 15, are held by pins 11 at a front end 12 of the receptacle 6. They can be removed from the dispenser at this position via an opening 16 having a diameter s which is larger than the diameter D of the capillaries 1. Alternatively, the capillaries 1 can be removed from the dispenser on the end face 12, e.g. by retracting the pins 11.

Figure 4:
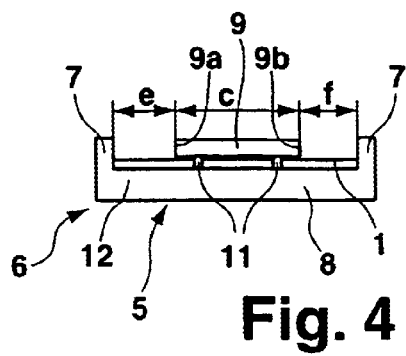

The dispenser of FIG. 4 has a central guiding member 9 which is disposed at separations c and d, respectively, from the U-shaped legs 7 of the receptacle 6 to define one free space between each of its longitudinal edges 9a,9b and the respective U-shaped leg 7 for removing two adhesive tapes (not shown) which are disposed at a separation from one another on the capillaries 1. The width of the adhesive tapes (not shown) approximately corresponds to the distance e, f between the central guiding member 9 and the U-shaped legs 7 of the receptacle 6. The separations e, f are preferably equal.

The dispenser improves the handling of the capillaries 1, since they are stored such that they do not break and can be removed from the dispenser with precise and constant orientation.

We claim:

1. A dispenser for a plurality of individual capillaries, each capillary having a capillary length and a capillary outer diameter, the plurality of capillaries bonded to an adhesive tape to be substantially parallel to each other, the capillaries disposed transverse to a longitudinal extension of the adhesive tape and projecting past the tape at both ends of the capillaries, the dispenser comprising:

a bottom;

a first side wall adjacent with adjacent to said bottom;

a second side wall adjacent to said bottom and extending substantially parallel to and at a first separation from said first side wall, said first separation being larger than said capillary length;

a top cooperating with said first and said second side walls and extending substantially parallel to and at a second separation from said bottom, said second separation being greater than said capillary outer diameter, said top having an elongated opening with a width greater than the width of the adhesive tape, wherein said first side wall, said second side wall, and said top are structured, dimensioned and disposed to define an elongated receptacle into which the capillaries can be inserted while in contact with the adhesive tape, wherein the adhesive tape can than be separated from the capillaries by removal through said elongated opening in said top;

a resiliently biased slider configured to urge the capillaries in said elongated receptacle towards a dispensing location.

2. The dispenser of claim 1, further comprising means, disposed at an end of said elongated receptacle facing away from said dispensing location, cooperating with said slider to arrest said slider for loading the capillaries into said elongated receptacle.

3. The dispenser of claim 1, wherein said bottom defines a longitudinal slot, wherein said slider comprises a guiding pin disposed in said longitudinal slot, a helical spring borne on said guiding pin, and a carriage cooperating with said guiding pin and said helical spring.

4. The dispenser of claim 1, further comprising means for winding and unwinding the capillaries with the adhesive tape about an axle, said winding and unwinding means having a helical spring acting on said axle, for loading into said receptacle.

5. The dispenser of claim 1, wherein said dispensing location is structured for removal of the capillaries from the dispenser in axial directions thereof.

6. The dispenser of claim 1, wherein said dispensing location has at least one discharge opening which is disposed at a level of the capillaries and which penetrates through at least one of said first side wall and said second side wall.

7. The dispenser of claim 6, wherein a diameter of said discharge opening corresponds approximately to a diameter of the capillaries.

8. The dispenser of claim 1, wherein said elongated opening extends along a central portion of said elongated receptacle.

9. The dispenser of claim 1, wherein said elongated opening consists essentially of a first opening strip and a second opening strip extending substantially parallel to and at a separation from said first opening strip, wherein the adhesive tape consists essentially of a first tape strip which can be removed through said first opening strip and a second tape strip which can be removed through said second opening strip.

\* \* \* \* \*

UNITED STATES PATENT AND TRADEMARK OFFICE
CERTIFICATE OF CORRECTION

PATENT NO. : 6,845,881 B1
DATED : January 25, 2005
INVENTOR(S) : Bigus, Hans Juergen et al.

It is certified that error appears in the above-identified patent and that said Letters Patent is hereby corrected as shown below:

Column 1,
Lines 9-11, please delete "Use of adhesive Tape for Handling, Transporting, and Storing Capillaries and Dispenser for Individual Capillaries on That Adhesive Tape"

Column 6,
Line 7, delete "adjacent with", first occurrence.
Line 24, insert -- and -- following "said top;".

Signed and Sealed this

Seventeenth Day of May, 2005

JON W. DUDAS
*Director of the United States Patent and Trademark Office*